United States Patent [19]

Mouzin et al.

[11] 4,456,614

[45] Jun. 26, 1984

[54] 3-AMINO-1-[(1,4-BENZODIOXAN)-2-YL-METHOXY]-2-PROPANOLS, PHARMACEUTICAL COMPOSITIONS THEREOF, AND THEIR USE AS MEDICAMENTS

[75] Inventors: Gilbert Mouzin, Castre; Henri Cousse, Castres; Pol Vilain, Labruguiere, all of France

[73] Assignee: Pierre Fabre S.A., Paris, France

[21] Appl. No.: 250,407

[22] Filed: Apr. 2, 1981

[30] Foreign Application Priority Data

Apr. 4, 1980 [FR] France ................................ 80 07719

[51] Int. Cl.³ .................. A61K 31/335; C07D 319/14
[52] U.S. Cl. ...................................... 424/278; 549/366
[58] Field of Search ........................ 549/366; 424/278

[56] References Cited

U.S. PATENT DOCUMENTS

| | | | |
|---|---|---|---|
| 3,324,143 | 6/1967 | Moed et al. | 549/366 |
| 3,340,266 | 9/1967 | Howe et al. | 549/366 |
| 3,444,210 | 5/1969 | Moed et al. | 549/366 |
| 3,472,874 | 10/1969 | Shapero et al. | 549/366 |

FOREIGN PATENT DOCUMENTS 37778 10/1981 European Pat. Off. ............ 549/366
2358142 10/1978 France .

*Primary Examiner*—Ethel G. Love
*Attorney, Agent, or Firm*—Gordon W. Hueschen

[57] ABSTRACT

The present invention concerns chemical compounds of the general formula:

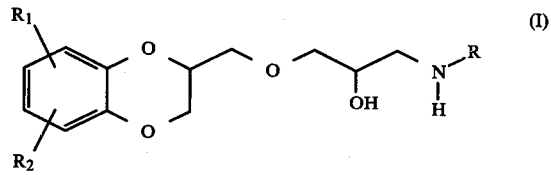

in which:

$R_1$ and $R_2$ may be identical or different and represent a hydrogen or halogen atom or else a lower alkyl, lower alkoxy, nitro or acetyl group and R represents a lower alkyl or lower aralkyl group, such as benzyl.

These compounds are useful in therapy for the treatment of hypertension and cardiac arrhythmia.

7 Claims, No Drawings

3-AMINO-1-[(1,4-BENZODIOXAN)-2-YL-METHOXY]-2-PROPANOLS, PHARMACEUTICAL COMPOSITIONS THEREOF, AND THEIR USE AS MEDICAMENTS

The present invention, developed at the PIERRE FABRE Research Center, has as its object new chemical compounds, their method of preparation and their use in therapy, particularly for the treatment of hypertension and arrythmias of various origins.

The invention also relates to pharmaceutical compositions containing these active principles and method of treating hypertension and arrythmias therewith.

The present invention refers to new chemical compounds having general formula I:

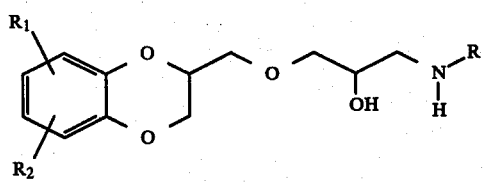

in which:

$R_1$ and $R_2$ may be identical or different and represent a hydrogen or halogen atom or else a lower alkyl, lower alkoxy, nitro or acetyl group and R represents a lower alkyl or a lower aralkyl group, such as benzyl, as well as their salts with therapeutically acceptable inorganic or organic acids.

Acids capable of leading to therapeutically acceptable salts of compounds of formula I are, for instance, hydrochloric acid, sulfuric acid, phosphoric acid, succinic acid, oxalic acid, tartaric acid, maleic acid and fumaric acid.

By lower alkyl radical there will be understood essentially linear or branched alkyl radicals containing from 1 to 8 carbon atoms and preferably 1 to 4 carbon atoms.

In accordance with the present invention, the new compounds of formula I can be prepared by a process which comprises the following two reaction steps:

1st Step

Preparation of the glycidyl ether of 2-hydroxymethyl benzodioxan

By condensation of epichlorhydrin with a 2-hydroxymethyl benzodioxan derivative of formula II in the presence of a base such as caustic soda and of a catalyst of quaternary ammonium type having the formula

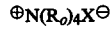

there is obtained the glycidyl ether of formula III

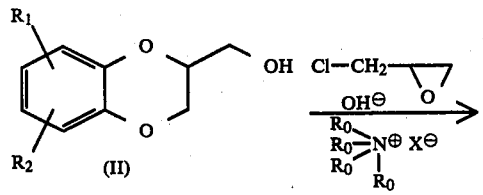

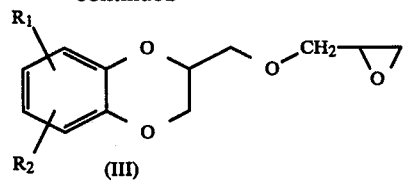

in which formulas the radicals $R_1$ and $R_2$ have the same meanings as those given previously with respect to formula I, $R_o$ represents a lower alkyl radical and $X^\ominus$ the anion of an acid, for instance $HSO_3^\ominus$ or $Hal^\ominus$.

The 2-hydroxymethyl benzodioxan derivatives of formula II which are used as synthesis intermediates can be prepared, for instance, by the method of J. AUGSTEIN et al.—J. Med. Chem. 8, 446 (1965).

2nd Step

By opening the intermediate epoxide of formula III by means of a primary amine of formula IV the derivatives of formula I are obtained:

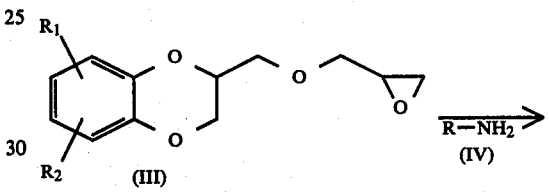

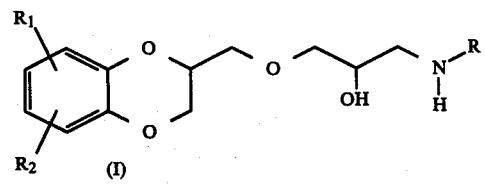

in which formulas the radicals R, $R_1$ and $R_2$ have the same meaning as given previously with respect to formula I.

The following chemical compounds and their manner of preparation are cited by way of illustration and not of limitation:

EXAMPLE 1

Preparation of 3-tertiobutylamino-1-[(1,4-benzodioxan)-2-yl methoxy]-2-propanol maleate (a) Preparation of (1,4-benzodioxan)-2-yl methyl glycidyl ether To a heterogenous mixture of 100 ml of epichlorhydrin, 100 ml of 50% caustic soda and 1.4 g of tetrabutylammonium hydrogen sulfate there are added, with good agitation, 16.6 g (0.1 mol) of 2-hydroxymethyl-1,4-benzodioxan.

The reaction is set aside for two hours at room temperature whereupon 100 ml of water and 200 ml of ethyl acetate are added. After settling and washing of the organic phase with water, a bicarbonate solution and then water saturated with sodium, it is dried over sodium sulfate.

After filtration and evaporation of the solvent the glycidyl ether is obtained in quantitative yield.

(b) Preparation of 3-tertiobutylamino-1-[1,4-benzodioxan)-2-yl methoxy]-2-propanol maleate To an iced solution of 21 ml (14.6 g-0.2 mol) of tertiobutylamine in 200 ml of methanol, there are added 50 mmols (14.25 g) of (1,4-benzodioxan)-2-yl methyl glycidyl ether.

After stirring for three hours at room temperature, the reaction mixture is brought to reflux for one hour. It is left overnight at room temperature and then evaporated to dryness. The residual oil is taken up with ethyl ether, washed three times with water and then dried over sodium sulfate. The resultant solution is filtered and treated with 6 g of maleic acid dissolved in 200 ml of ethyl ether. It is iced and filtered; the crude crystals obtained are recrystallized from a mixture of ethyl acetate and isopropyl ether.

The product of the formula

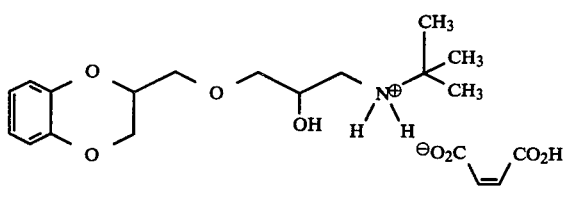

is recovered with a yield of 75%.

Empirical formula: $C_{20}H_{29}NO_8$ Molecular weight: 411.4 Crystals: White Melting point: 90° C.
Plate chromatography:
  Solvent: chloroform-methanol-ammonia 80/18/2
  Support: Silica gel 60 F 254 Merck
  Development: UV and iodine
  Rf: 0.5
  Solubility: 10% soluble in water.

EXAMPLE 2

Preparation of 3-tertiobutylamino-1-[(6-methyl-1,4-benzodioxan)-2-yl methoxy]-2-propanol hydrochloride In a manner similar to that described in Example 1 but using 2-hydroxymethyl-6-methyl-1,4-benzodioxan, tertiobutylamine and hydrochloric acid as salinifying agent, there is obtained the product of the formula:

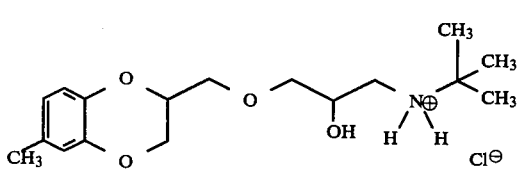

EXAMPLE 3

Preparation of 3-tertiobutylamino-1-[(5-methyl-1,4-benzodioxan)-2-yl methoxy]-2-propanol hydrochloride In a manner similar to the preceding example but using 2-hydroxymethyl-5-methyl-1,4-benzodioxan, there is obtained the product of the formula:

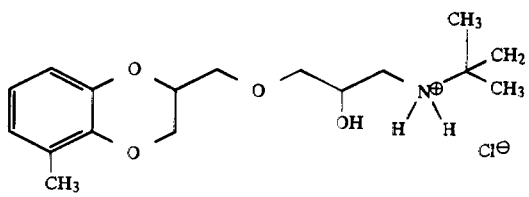

EXAMPLE 4

Preparation of 3-tertiobutylamino-1-[(7-methyl-1,4-benzodioxan)-2-yl methoxy]-2-propanol hydrochloride In a manner similar to that described in Example 1 but using 2-hydroxymethyl-7-methyl-1,4-benzodioxan, tertiobutylamine and hydrochloric acid as salinifying agent, there is obtained the product of the formula:

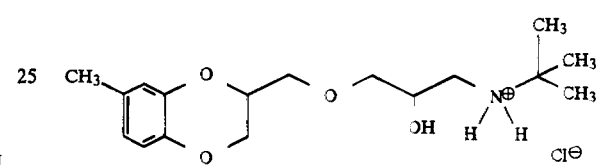

EXAMPLE 5

Preparation of 3-tertiobutylamino-1-[(8-methyl-1,4-benzodioxan)-2-yl methoxy]-2-propanol hydrochloride In a manner similar to that described in Example 1 but using 2-hydroxymethyl-8-methyl-1,4-benzodioxan, tertiobutylamine and hydrochloric acid as salinifying agent, there is obtained the product of the formula:

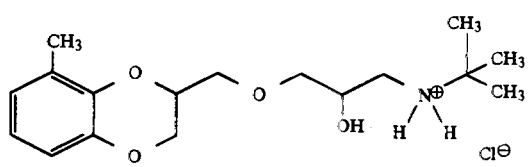

EXAMPLE 6

Preparation of 3-isopropylamino-1-[(5-chloro-1,4-benzodioxan)-2-yl methoxy]-2-propanol fumarate In a manner similar to that described in Example 1 but using 2-hydroxymethyl-5-chloro-1,4-benzodioxan, isopropylamine and fumaric acid as salinifying agent, there is obtained the product of the formula:

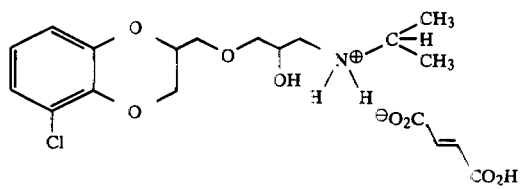

EXAMPLE 7

Preparation of 3-isopropylamino-1-[(7-chloro-1,4-benzodioxan)-2-yl-methoxy]-2-propanol fumarate In a manner similar to that described in Example 1 but using 2-hydroxymethyl-7-chloro-1,4-benzodioxan, isopropyl amine and fumaric acid as salinifying agent there is obtained the product of the formula:

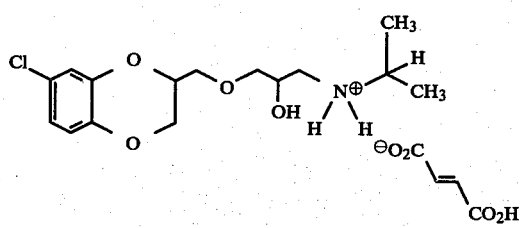

EXAMPLE 8

Preparation of isopropyl-3-amino-1-[(7-nitro-1,4-benzodioxan)-2-yl-methoxy]-2-propanol hydrochloride In a manner similar to that described in Example 1 but using 2-hydroxymethyl-7-nitro-1,4-benzodioxan, isopropyl amine and hydrochloric acid as salinifying agent, there is obtained the product of the formula:

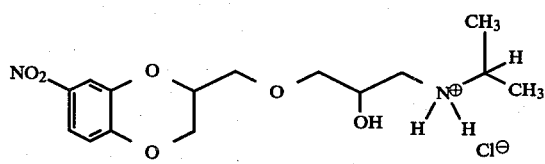

EXAMPLE 9

Preparation of 3-tertiobutylamino-1-[(7-methoxy-1,4-benzodioxan)-2-yl-methoxy]-2-propanol hydrochloride In a manner similar to that described in Example 1 but using 2-hydroxymethyl-7-methoxy-1,4-benzodioxan, tertiobutyl amine and hydrochloric acid as salinifying agent, there is obtained the product of the formula:

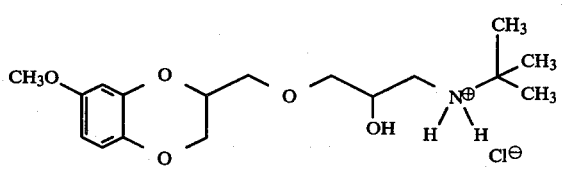

EXAMPLE 10

Preparation of 3-tertiobutylamino-1-[(6-acetyl-1,4-benzodioxan)-2-yl-methoxy]-2-propanol maleate In a manner similar to Example 1 but using 2-hydroxymethyl-6-acetyl-1,4-benzodioxan, tertiobutyl amine and maleic acid as salinifying agent, there is obtained the product of the formula:

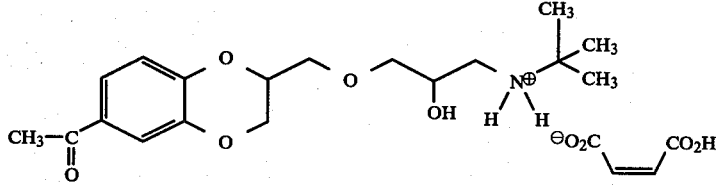

EXAMPLE 11

Preparation of 3-tertiobutylamino-1-[(5,7-dimethyl-1,4-benzodioxan)-2-yl-methoxy]-2-propanol hydrochloride In a manner similar to that described in Example 1 but using 2-hydroxymethyl-5,7-dimethyl-1,4-benzodioxan, tertiobutylamine and hydrochloric acid as salinifying agent, there is obtained the product of the formula:

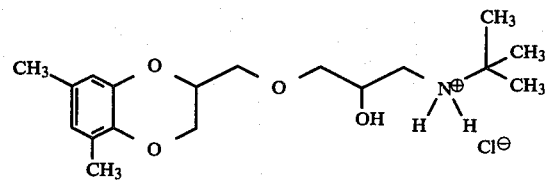

EXAMPLE 12

Preparation of 3-tertiobutylamino-1-[(6,7-dichloro-1,4-benzodioxan)-2-yl-methoxy]-2-propanol hydrochloride In a manner similar to that described in Example 1 but using 2-hydroxymethyl-6,7-dichloro-1,4-benzodioxan, tertiobutylamine and hydrochloric acid as salinifying agent, there is obtained the product of the formula:

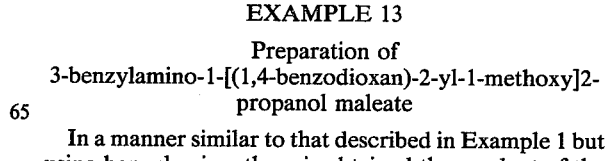

EXAMPLE 13

Preparation of 3-benzylamino-1-[(1,4-benzodioxan)-2-yl-1-methoxy]2-propanol maleate In a manner similar to that described in Example 1 but using benzylamine, there is obtained the product of the formula:

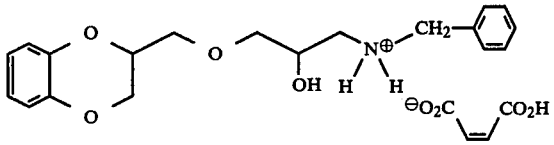

The new compounds of formula I of the present invention, which have good anti-hypertension and anti-arrhythmic pharmacological properties can also be used in therapy, in particular for the treatment of hypertension and arrythmias of various origin.

It has been possible to establish these pharmacological properties by means of the following experiments.

EXPERIMENTS

(A) Toxicology

The chemical compounds described above were subjected to toxicity tests. The study of the toxicity was carried out on the conventional mouse weighing from 20 to 22 g.

The substances were administered intravenously and orally. The $LD_{50}$ was calculated in accordance with the method of G. KARBER, Arch. Exptl. Pathol. Pharmacol., 162, 1931, 480.

The $LD_{50}$ values by intravenous injection are between 30 and 100 mg/kg. By oral administration the $LD_{50}$ values are between 600 and 900 mg/kg.

(B) Pharmacological Study

The pharmacological experiments to which the chemical compounds forming the object of the invention were subjected made it possible to show the following pharmacological properties:
  anti-arrhythmic
  beta blocking
  anti-hypertensive.

In order to illustrate these tests, we describe below the results obtained with the compound of Example 1, namely: 3-tertiobutylamino-(1,4-benzodioxan)-2-yl-1-methoxy-2-propanol maleate.

(1) Determination of anti-arrhythmic properties (a) Action with respect to ventricular tachycardia of digitalic origin (LUCHESI and HARDMAN—J. Pharmacol. exp. Ther., 1961, No. 132, pages 372 to 81).

Method: Creation of a stable ventricular tachycardia in ten dogs (anesthetized) by successive intravenous injections of ouabain.

Results: The compound 3-tertiobutylamino-1-[(1,4-benzodioxan)-2-yl-methoxy]-2-propanol maleate, in doses of 2 and 5 mg/kg, opposes ectopic rhythm in all the animals.

The period of activity is more than 30 minutes in 80% of the cases.

(b) Influence on an auricular tachycardia produced by aconitine.

Method: (D. SCHERF-Proc. Soc. exp. Biol., 1947, 64, 233). A tachycardia is caused in dogs by intramural injection of aconitine in the right atrium near the sinusoidal node.

The rhythm is increased in proportions of 80 to 100%. The auriculo-ventricular tracks show normal permeability, the ventricles are driven at the same frequency.

Results: The compound 3-tertiobutylamino-1-[(-1,4-benzodioxan)-2-yl-methoxy]-2-propanol maleate, in a dose of 5 mg/kg in vitro, reduces auricular tachycardia substantially and lastingly (% reduction 60%—progressive return to the pathological rhythm, but the effect of the product persists for 30 minutes after injection).

(c) Effect on the frequency of spontaneous flutterings of the isolated atrium.

Method: Rabbit right atrium in survival in a Ringer-Locke's solution. The substances to be studied are introduced into the tank (at the rate of 0.5 and 1 mg per 100 ml) and remain in contact with the myocardial tissue for 24 minutes.

Results: The compound 3-tertiobutylamino-1-[(1,4-benzodioxan)-2-yl-methoxy]-2-propanol maleate has definitely a less negative chronotropic effect than dihydroquinidine.

Percentage of reduction of the frequency after 24 minutes:

| | |
|---|---|
| Dihydroquinidine (1 mg) | −35% |
| Compound 3-tertiobutylamino-1-[(1,4-benzodioxan)-2-yl-methoxy]-2-propanol maleate (1 mg) | −16% |

(d) Activity on the electrosystolic entrainment of the isolated rabbit atrium (G. S. DAWES-Pharmacol. Rev., 4, 43–84, 1952).

Method: Rabbit right atrium in a Ringer-Locke's solution.

After determination of the threshold voltage for the entrainment of the muscle, the latter is subjected to frequencies which increase in successive steps until obtaining a maximum frequency for which the tissue is incapable of responding to the stimuli.

The product is added to the bath. Three electric entrainments are effected in the following 25 minutes. The experiment is then continued for one hour after the rinsing of the tank.

Results: The compound 3-tertiobutylamino-1-[(1,4-benzodioxan)-2-yl-methoxy]-2-propanol maleate extends the functional refractory period of the isolated atrium in the same way as dihydroquinidine.

Percentage decrease of threshold:

| | |
|---|---|
| Dihydroquinidine (0.5 mg) | 45% |
| 3-tertiobutylamino-1-[(1,4-benzodioxan)-2-yl-methoxy]-2-propanol maleate (0.5 mg) | 51% |

(2) Search for an inhibitory property of the adrenergic receptors (O. DUNLOP, P. SHANKS, Brit J. Pharmacol., 1968, 32, pages 201–218).

Method: Isoprenaline tachycardia in dogs. Simultaneous recording of the heart rate and of the arterial pressure.

Results: The compound 3-tertiobutylamino-1-[(1,4-benzodioxan)-2-yl-methoxy]-2-propanol maleate significantly reduces the isoprenaline tachycardia starting with a dose of 1 mg/kg intravenously.

At 5 mg/kg, the beta-blocking effect is substantial and cardioselectivity is noted.

(3) Systemic effects in dogs

Doses used: 1, 2 and 5 mg/kg
Parameters noted:
  arterial pressure
  heart rate respiratory rate
left intraventricular pressure
contractability index
flows:
  coronary
  renal
  vertebral
  femoral
  carotidian The compound 3-tertiobutylamino-1-[(1,4-benzodioxan)-2-yl-methoxy]-2-propanol maleate has little impact on the cardiovascular system. It nevertheless decreases the force of cardiac contraction and the peripheral resistances, thus providing a group of properties adapted to combat hypertension.

(4) Effect on the central nervous system

Potentialization of the barbiturate and chloralhydrate anesthesia in mice.
Dose: 100 mg/kg
Results: nothing to report
Anticonvulsant property (G. CHEN and R. PORTMAN, A.M.A. Arch. Neurol. Psychiat., 68, 498, 1952).

The compound 3-tertiobutylamino-1-[(1,4-benzodioxan)-2-yl-methoxy]-2-propanol maleate does not protect mice from toxicity of pentetrazole administered subcutaneously (compound of 3-tertiobutylamino-1-[(1,4-benzodioxan)-2-yl-methoxy]-2-propanol maleate—orally—100 mg/kg).

Anti-depressant properties (W. J. LANG and S. GORSHORN Arch. Int. Pharmacodyn., 142, 457, 1963).
No potentialization of toxicity to yohimbine in mice.

(5) Miscellaneous effects

Local anesthesia: test of J. Regnier—Doctoral Dissertation, Med., 203 pages, Bruilliard St Dizier, 1929.
A 1% solution shows local anesthetic properties superior to Lidocaine.

Diuretic effect (W. LIPSCHITZ J. Pharmacol. Exp. Ther., 79, 97, 1943) in rats.
The compound 3-tertiobutylamino-1-[(1,4-benzodioxan)-2-yl-methoxy]-2-propanol maleate does not have any diuretic power.
Dose: 100 mg/kg orally.

| | |
|---|---|
| Urinary excretion with compound of 3-tertiobutylamino-1-[(1,4-benzodioxan)-2-yl-methoxy]-2-propanol maleate | 35% |
| Control | 28% |

(C) Therapeutic Applications

In view of their pharmacological properties and their low toxicity, these compounds and more particularly the compound 3-tertiobutylamino-1-[(1,4-benzodioxan)-2-yl-methoxy]-2-propanol maleate can be used in therapy for the treatment of cardiac disturbances and more particularly hypertension.

These compounds can be used in the form of pharmaceutical compositions in which the active compound is mixed with pharmaceutically acceptable non-toxic diluent vehicles which facilitate their bioavailability.

These compounds can be administered parenterally, intravenously or by mouth or rectal route. The doses of administration may vary in rather large proportions as a function of the method of administration selected as well as the type and seriousness of the ailment to be treated.

The compounds may, for instance, be in the form of tablets, capsules, suppositories, aqueous or oil solutions, aqueous or oil suspensions, emulsions, dispersible powders or solutions in injectable oil or aqueous suspensions.

We claim:

1. A compound of formula I:

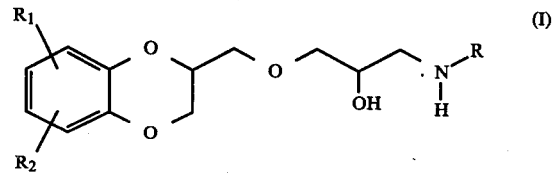

in which:
R₁ and R₂ may be identical or different and represent a hydrogen or halogen atom or a lower alkyl, lower alkoxy, nitro or acetyl group, and
R represents a lower alkyl or lower aralkyl group, or a pharmaceutically acceptable salt thereof with an inorganic or organic acid.

2. A compound of claim 1, wherein R represents an isopropyl or tertiobutyl radical.

3. A compound of claim 1, selected from:
3-tertiobutylamino-1-[(1,4-benzodioxan)-2-yl-methoxy]-2-propanol maleate;
3-tertiobutylamino-1-[(6-methyl-1,4-benzodioxan)-2-yl-methoxy]-2-propanol hydrochloride;
3-tertiobutylamino-1-[(5-methyl-1,4-benzodioxan)-2-yl-methoxy]-2-propanol hydrochloride;
3-tertiobutylamino-1-[(7-methyl-1,4-benzodioxan)-2-yl-methoxy]-2-propanol hydrochloride;
3-tertiobutylamino-1-[(8-methyl-1,4-benzodioxan)-2-yl-methoxy]-2-propanol hydrochloride;
3-isopropylamino-1-[(5-chloro-1,4-benzodioxan)-2-yl-methoxy]-2-propanol fumarate;
3-isopropylamino-1-[(7-chloro-1,4-benzodioxan)-2-yl-methoxy]-2-propanol fumarate;
3-isopropylamino-1-[(7-nitro-1,4-benzodioxan)-2-yl-methoxy]-2-propanol hydrochloride;
3-tertiobutylamino-1-[(7-methoxy-1,4-benzodioxan)-2-yl-methoxy]-2-propanol hydrochloride;
3-tertiobutylamino-1-[(6-acetyl-1,4-benzodioxan)-2-yl-methoxy]-2-propanol maleate;
3-tertiobutylamino-1-[(5,7-dimethyl-1,4-benzodioxan)-2-yl-methoxy]-2-propanol hydrochloride;
3-tertiobutylamino-1-[(6,7-dichloro-1,4-benzodioxan)-2-yl-methoxy]-2-propanol hydrochloride, and
3-benzylamino-1-[(1,4-benzodioxan)-2-yl-methoxy]-2-propanol maleate.

4. A method of treating hypertension and arrhythmia comprising the step of administering to a subject suffering from such a disturbance an effective antihypertensive or antiarrhythmic amount of a compound according to any of claims 1, 2 or 3.

5. A pharmaceutical composition, suitable for use as an antihypertensive or antiarrhythmic agent, characterized by the fact that it contains, as active principle, an effective antihypertensive or antiarrhythmic amount of at least one compound of any of claims 1, 2 or 3, together with a pharmaceutically-acceptable vehicle or carrier therefor.

6. A compound of claim 1 which is 3-tertiobutylamino-1-[(1,4-benzodioxan)-2-yl-methoxy]-2-propanol pharmaceutically-acceptable acid addition salt.

7. A compound of claim 1 which is 3-tertiobutylamino-1-[(1,4-benzodioxan)-2-yl-methoxy]-2-propanol maleate.

* * * * *